(12) United States Patent
Colman et al.

(10) Patent No.: US 6,437,316 B1
(45) Date of Patent: Aug. 20, 2002

(54) FLUID ANALYZER WITH TUBE CONNECTOR VERIFIER

(75) Inventors: Joshua L. Colman, Ramat Shlomo; Amnon Menachem, Jerusalem, both of (IL)

(73) Assignee: Oridion Medical Ltd. (IL)

( * ) Notice: Subject to any disclaimer, the term of this patent is extended or adjusted under 35 U.S.C. 154(b) by 0 days.

(21) Appl. No.: 08/961,013

(22) Filed: Oct. 30, 1997

(30) Foreign Application Priority Data

Nov. 4, 1996 (IL) ................................................ 119562

(51) Int. Cl.$^7$ ................................................ H01J 40/14
(52) U.S. Cl. ................................ 250/222.1; 250/559.3
(58) Field of Search ................................ 356/301, 410, 356/440, 246; 250/559.4, 559.3, 221, 222.1, 458.1, 461.1, 462.1, 465.1, 466.1, 343; 285/93; 403/27; 600/532, 533, 534, 535, 536, 537, 543

(56) References Cited

U.S. PATENT DOCUMENTS

| | | | |
|---|---|---|---|
| 3,795,805 A | | 3/1974 | Swanberg et al. |
| 3,797,936 A | | 3/1974 | Dimitriadis |
| 4,079,605 A | | 3/1978 | Bartels |
| 4,374,397 A | * | 2/1983 | Mir |
| 4,511,251 A | * | 4/1985 | Falcoff et al. ............... 356/246 |
| 4,593,192 A | | 6/1986 | Slattery et al. |
| 4,612,670 A | | 9/1986 | Henderson |
| 4,834,706 A | | 5/1989 | Beck et al. |
| 5,095,210 A | | 3/1992 | Wheatley et al. |
| 5,200,794 A | | 4/1993 | Nishiguma et al. |
| 5,369,529 A | | 11/1994 | Kuo et al. |
| 5,404,218 A | * | 4/1995 | Nave et al. |
| 5,422,565 A | | 6/1995 | Swanson |
| 5,444,526 A | | 8/1995 | Echapare Ibarrola et al. |
| 6,089,105 A | * | 7/2000 | Ricciardelli ............... 73/861.52 |

FOREIGN PATENT DOCUMENTS

| | | |
|---|---|---|
| DE | 4310855 | 10/1994 |
| EP | 0679367 | 11/1995 |
| EP | 0742027 | 11/1996 |

\* cited by examiner

Primary Examiner—F. L. Evans
(74) Attorney, Agent, or Firm—Hoffman, Wasson & Gitler

(57) ABSTRACT

Apparatus for analyzing fluid supplied to it through a tube, comprising an analyzing instrument within an enclosure, a first connector attached to the tube and having an end face, a second connector, mating with the first connector and attached to the enclosure, a pair of optical fibers disposed inside the enclosure, a first end of each of the fibers is mounted in the second connector, there is a clear optical path between the end face of each of the first ends of the fibers and at least one common point on the end face. A light source is optically coupled to the second end of a first one of the pair of fibers, and a light detector optically coupled to the second end of the second one of the pair of fibers.

86 Claims, 4 Drawing Sheets

LONGITUDINAL SECTION

END VIEW

FLUID ANALYZER WITH TUBE CONNECTOR VERIFIER

FIELD AND BACKGROUND OF THE INVENTION

The present invention concerns a system for verifying the presence and identity of a tube connector connected to an instrument and, more particularly, an electro-optical method and device to determine whether a tube assembly has been connected to a fluid analyzing instrument and, if so, whether it belongs to a certain class of such tube assemblies.

The particular application for which the present invention will be described is that of a capnograph, which is an instrument for analyzing exhaled air. A capnograph is used by sampling air exhaled by a patient, by means of a small tube, also called sampling line, one end of which is, for example, connected to an air passageway of a respirator or to a cannula attached to the patient's nostrils; the tube is connected at its other end, through a special connector, to the analyzing instrument. The tube assembly, especially of the type that is the subject of the present invention, often includes a filter or other means for removing moisture and mucus; alternatively, there may be a filter built into the capnograph or supplied separately, to be connected to the tube. The complete tube assembly, including the filter and the connector, is usually of the disposable type and is replaced for every patient tested.

A typical connector, also referred to as a luer, is depicted in FIG. 1, which shows the two members, one male and one female, separated; each member is shown in an isometric view and in a longitudinal section. The shape of the connector, which is essentially round, as depicted in Fig. 1, is standardized throughout the industry, so that tube assemblies of various manufacturers may be interchangeably used with any analyzing instrument. Thus, the manufacturer of a particular type of analyzing instrument has generally no control over which type of tube and filter will be used with his instrument in practice. For reasons of optimal functioning of the instrument, as well as for commercial reasons, the manufacturer of an analyzing instrument may want to exert such control. In particular, he may want to stipulate that only a certain class of tube assemblies be connected to, and used with, his instrument. Such a class may, for example, consist of tube assemblies that include a filter, in general, or such that are manufactured directly by him or to his specifications or under his supervision or license. in particular.

One way to enforce this stipulation would be to use some unique interlocking key arrangement between the connector and the instrument. Such an arrangement would, however, be incompatible with the standard connector shape being used throughout and would require of the operator, when connecting and disconnecting the tube, different motions than those to which he is used.

Another way of enforcing the stipulation is to have a system by which the correct tube assembly would be identified as such by the instrument, whereupon its operation would be enabled, and to disable the instrument otherwise. A side benefit of such an arrangement would be that the instrument would be prevented from operation also when no tube is connected at all or when even a correct tube is improperly connected, thus avoiding damage to sensitive parts of the instrument and also causing incorrect readings. Yet another purpose may be served by such a system, namely identifying the tube assembly as belonging to one of a number of classes and informing the instrument of the particular identity detected, so as to enable it to automatically operate differently for the different classes.

There are known several types of means for effecting such identification. One type is electro-mechanical, whereby the connector would have one or more protrusions or notches at its end. which would engage appropriately placed levers that activate micro-switches. This type of means is impractical, because of the small dimensions of the connector pair and the little space available at the surrounding instrument panel. Another type of means is electrical, whereby the connector would have one or more conductive paths at its end, which would complete the circuit between appropriately placed contacts. This type of means is impractical, because of the dampness prevalent in the immediate surroundings.

There is thus a widely recognized need for, and it would be highly advantageous to have, a fluid analysis system that includes the capability of determining that a tube assembly has been properly connected to the analyzing instrument and that the tube is of a certain class. Such a capability must be compatible with the standard shape of connectors being used, as well as with the medical environment, must be reliable and must preferably be inexpensive—at least with regard to the fabrication of the disposable tube assembly.

SUMMARY OF THE INVENTION

The present invention successfully addresses the aforementioned needs by providing an air analysis system in which the presence and classification of a connected tube assembly can be conveniently and reliably detected.

The present invention discloses a novel modification of an air analysis system, whereby the presence of a tube connector of an acceptable class and its proper placement with respect to a mating connector, is ascertained by making the end of the connector appropriately reflective and by shining light thereon and detecting the light reflected thereof.

More specifically, the system of the present invention provides for a specularly reflective surface on the end of the tube connector of the acceptable class and for a pair of optical fibers mounted in the mating connector so that when, and only when, that tube connector is correctly positioned, a sufficient portion of light emitted from the end of one fiber is reflected into the end of the other fiber. The emitted light originates from a pulsed LED, optically coupled to the first fiber. The light reflected into the other fiber is detected by means of a photo-diode connected to a circuit that includes a comparator. The latter outputs a binary signal that can be used to enable or disable essential components of the analyzing instrument.

In an alternative configuration, the end of the tube connector has a fluorescent or phosphorescent material, which can be stimulated by the light emitted from the first fiber to re-emit light of spectral chareteristics different from those of the LED. A portion of the re-emitted light is collected by the second fiber and is passed through a spectrally selective filter, then detected as in the first configuration.

According to the present invention there is provided an apparatus for analyzing fluid supplied to it through a tube and a system for verifying the proper connection of the tube thereto and for classifying the tube, comprising:

an analyzing instrument within an enclosure;.

a first connector attached to the tube and having an end face;

a second connector, mating with the first connector and attached to the enclosure;

a pair of optical fibers disposed inside the enclosure, a first end of each of the fibers being mounted in the second connector so that, when the first connector is properly mated with the second connector, there is a clear optical path between the end face of each of the first ends of the fibers and at least one common point on the end face;

a light source optically coupled to the second end of a first fiber; and a light detector optically coupled to the second end of the second fiber.

According to further features in preferred embodiments of the invention described below, the end face is essentially specularly reflective over at least an annular portion thereof, the analyzing instrument is operative only upon reception of an enabling signal and further comprises an electric circuit connected to the light detector, the circuit being configured so that only if a substantial portion of any light emitted from the first end of one of the fibers is reflected by the annular portion of the end face into the first end of the other one of the fibers, will the circuit output the enabling signal to the analyzing instrument.

Preferably, the light source emits light in a narrow band of wavelengths and the apparatus further includes an optical filter, essentially transmissive of the narrow band of wavelengths and disposed in the path of the light transmitted through the second fiber. According to a modification of the preferred embodiment, the reflectivity of the end face is spectrally selective and the light source emits light in a narrow band of wavelengths, or there is a spectrally selective optical filter disposed in the path of the light transmitted through the second fiber.

According to another configuration, the end face is coated with a fluorescent or phosphorescent material, the light source emits light in a first band of wavelengths, such that stimulate the fluorescent or phosphorescent material to emit light in a second band of wavelengths, and the apparatus further includes an optical filter, essentially transmissive of at least one wavelength of the second band and disposed in the path of the light transmitted through the second fiber. According to a modification of this configuration, the second band of wavelengths is different among a plurality of types of the material and the optical filter of a particular apparatus is transmissive of the band corresponding to only one type.

According to further features in the described second configuration, the light source emits light as a first train of pulses and the circuit further includes a synchronous detector that is fed with a multiplying signal formed as a second train of pulses, the two trains of pulses having equal rates and the second train being delayed with respect to the first train.

There is also disclosed herein a method for verifying the proper connection of a tube to a fluid analyzing instrument and for classifying the connected tube, utilizing a system essentially as disclosed herein.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of a system for detecting the presence of a tube connector at the input of an instrument and for identifying it as belonging to a certain class, so as to affect a decision process in the instrument.

Specifically, the present invention can be used to verify that an acceptable type of tube assembly has been properly connected to the panel of a capnograph.

The principles and operation of a connector identifier according to the present invention may be better understood with reference to the drawings and the accompanying description.

Figure 1:
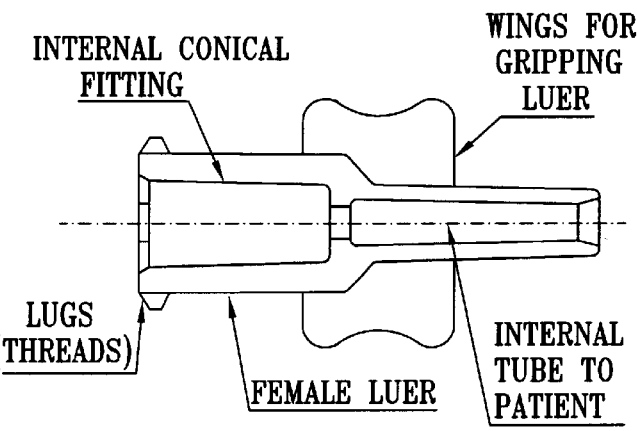
FIG. 1 is an illustration of a typical tube connector within a system that is the subject of the present invention.
Figure 1:
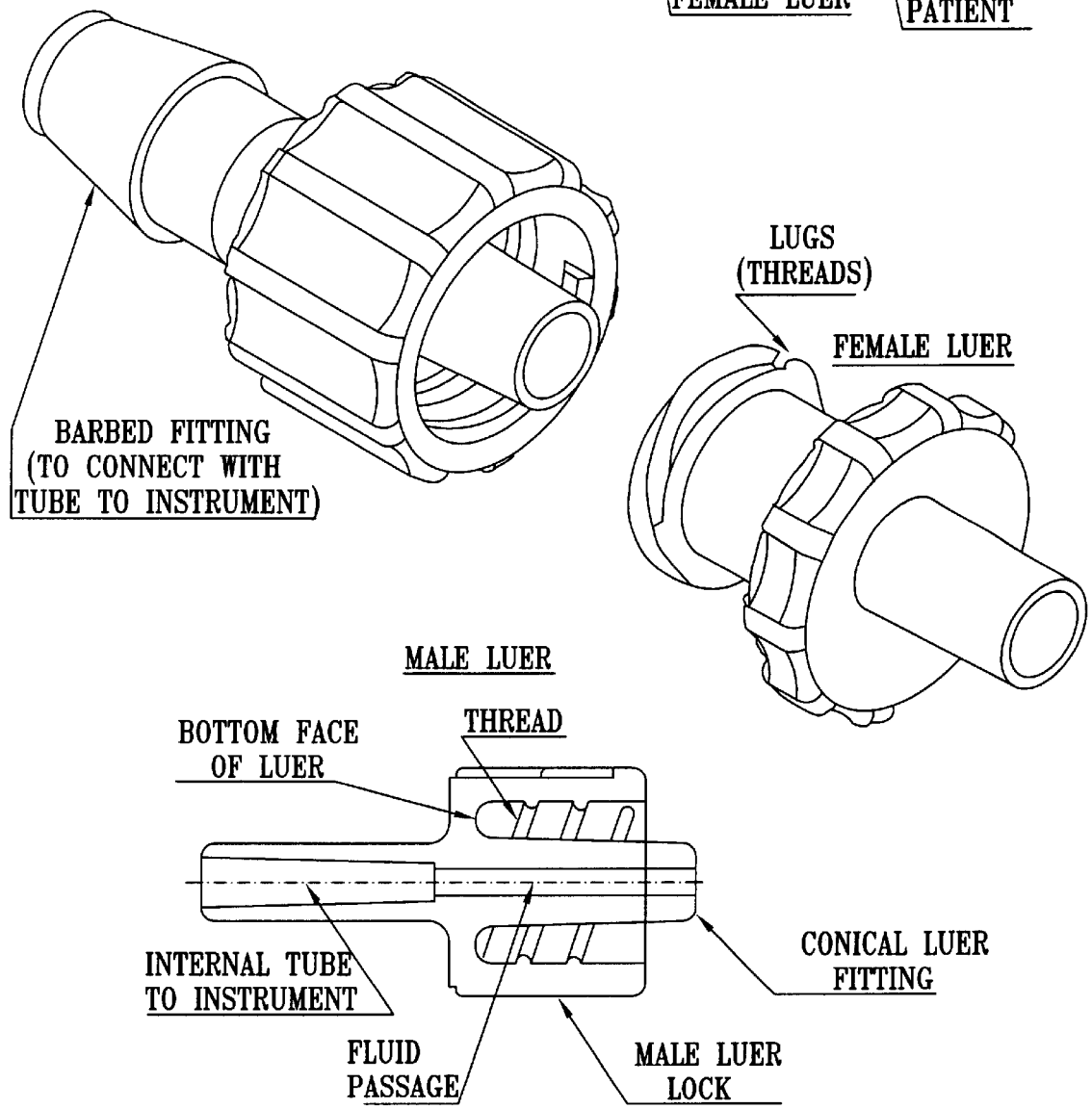
Figure 2:
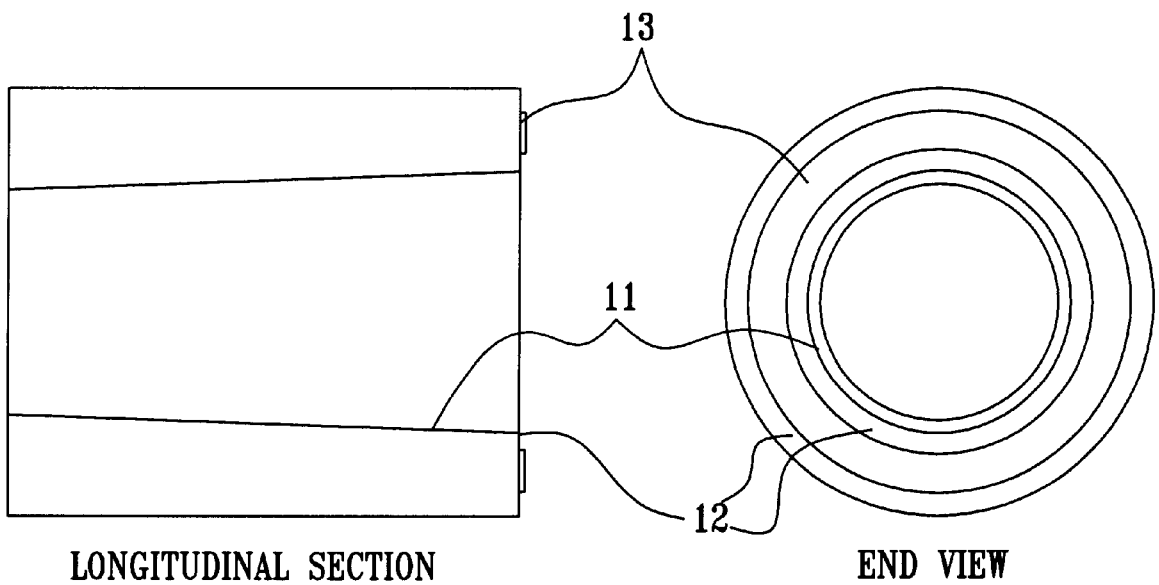
FIG. 2 is an orthogonal drawing of the connector of FIG. 1, modified according to the present invention.

Referring now to the drawings, FIG. 2 illustrates the essential part of the female member of the tube connector, modified according to a preferred embodiment of the invention. Basically, this is the standard female connector member (which will be referred to herebelow simply as a connector), as depicted in FIG. 1), typified by a slightly conical inner wall 11. The modification calls for the annular face 12 of its end (which is the end closest to the instrument panel) to be specularly reflective to light. The reflectivity may be obtained, for example, by coating the surface with a suitable reflective layer 13 or by polishing the surface to a glossy finish. A preferred method is to hot-press (or stamp) a reflective foil called Foil SLNM, available from Kurz Ltd, Germany; it is particularly suitable when the connector material is made of ABS. As will be seen herebelow, the reflective surface need not extend over the entire width of end face 12, but it must form a complete annular ring, since the luer may be connected to the panel in any angular orientation. A female connector with such a reflective annular surface on its end face will be referred to herebelow as a proper connector, and any other connector—as an improper connector.

Figure 3:
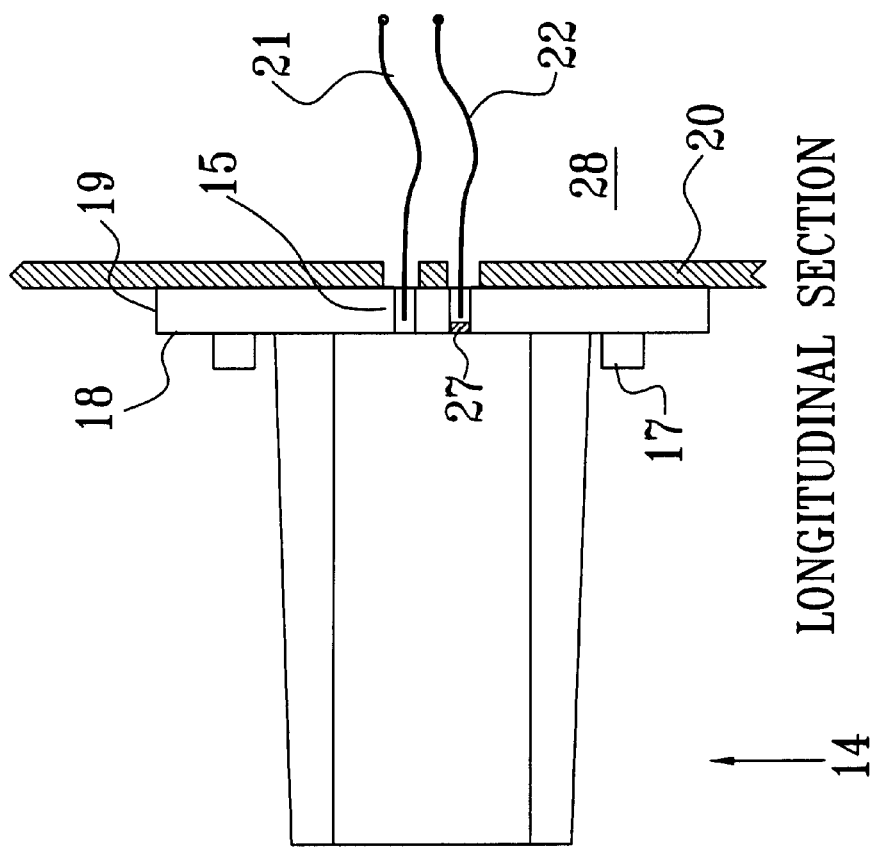
FIG. 3 is an orthogonal drawing of a connector mating with that of FIG. 2, modified according to the present invention.
Figure 3:
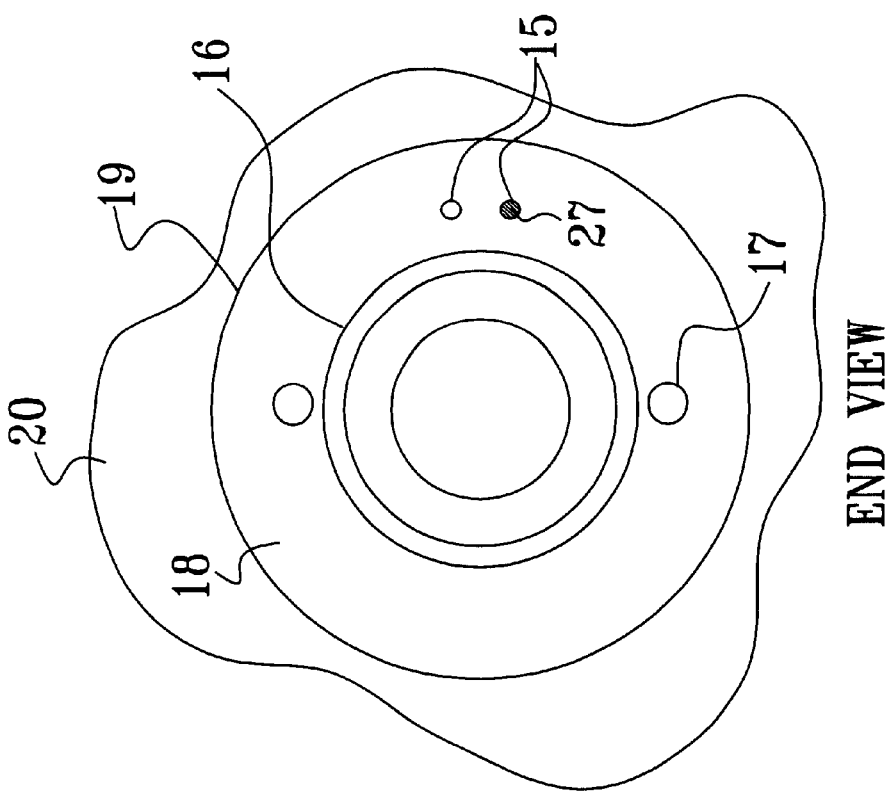

FIG. 3 shows a face-on view of the essential part of the matching male connector member 14, which is mounted on the panel 20 of the analyzing instrument 28; the central, slightly conical protrusion 16 fits inside the end of female connector 10 of FIG. 2 in such a manner that end face 12 of connector 10 is parallel to, and at a certain distance from, the annular surface 18 of male connector 14 that surrounds central protrusion 16. Through the back-plate 19 of male connector 14 there have been drilled two small holes 15, at a mutual distance of about 1.5 mm center-to-center, so that they form openings that face end face 12. Inside each hole 15 is mounted, respectively, an end of one of two optical fibers 21 and 22 that run inside the instrument. The fibers are mounted so that their end faces are flush with, or slightly sunk behind, annular face 18 of back-plate 19.

Figure 4:
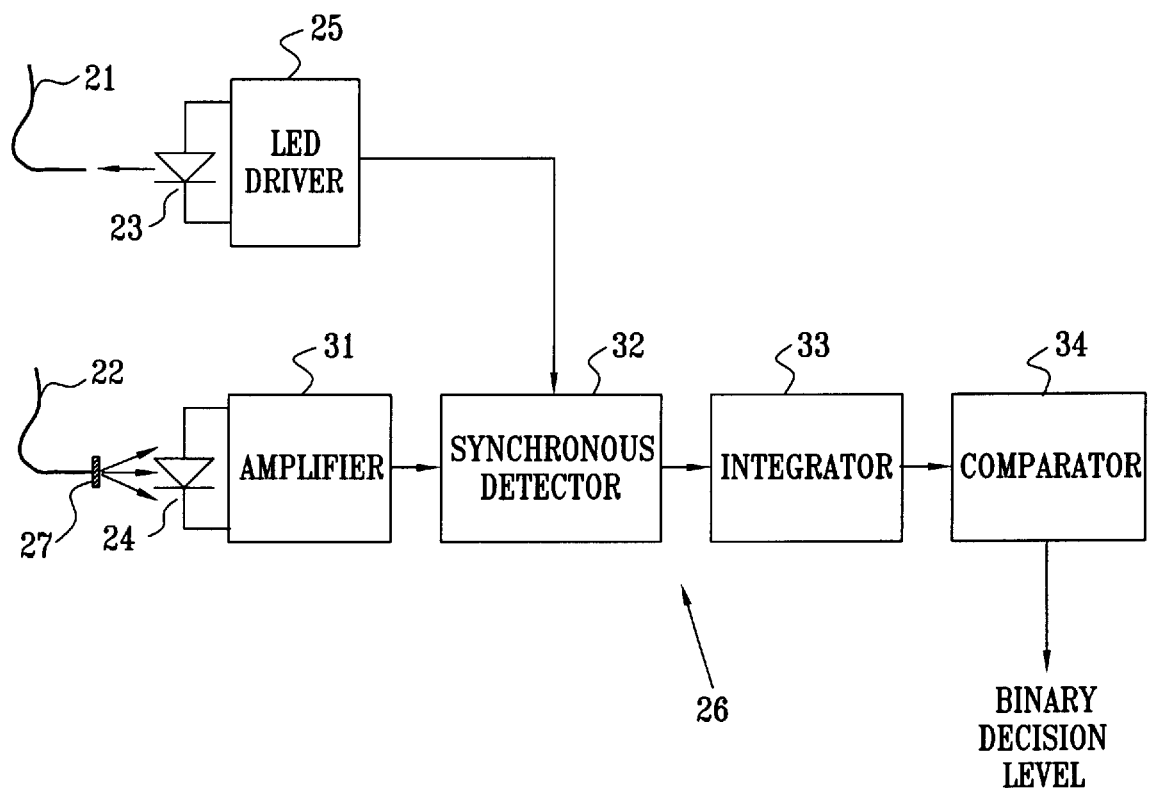
FIG. 4 is a schematic block diagram of an electric circuit according to a preferred embodiment of the present invention.

Reference is now made to FIG. 4, which is a schematic block diagram of an electronic circuit according to a preferred embodiment of the present invention, for generating and processing the optical signals transmitted to, and received from the connector pair.

The other end of fiber 21 is optically coupled to a light-emitting diode (LED) 23, while the other end of fiber 22 is optically coupled to a photodiode (PD) 24. Both LED 23 and PD 24 are mounted at a convenient location inside the instrument and are, respectively, connected to electric circuits 25 and 26. Electric circuit 25 generates a train of current pulses, at a rate of, say, approximately 1 kHz, which are driven through LED 23 and cause it to emit corresponding light pulses. The pulse train frequency is chosen so that this light can be easily discriminated from ambient light, including artificial lighting (which usually has power line frequencies and their harmonics). These light pulses are transmitted through fiber 21 and emitted at its end that is mounted in connector 14. If a proper female connector 10 is in place, its reflective end face 12 reflects an appreciable portion of the emitted pulsed light into the adjacent end of fiber 22, which transmits it to PD 24. This reflected and retransmitted light is detected by PD 24, which converts it to corresponding current pulses in circuit 26. It is noted that, according to standards for the dimensions of the connectors, the distance between end face 12 and surface 18 may be between 0.6 and 1.8 mm and this assures proper coupling of light between the fibers by specular reflection off the end face; however, in order to assure that the distance is not less than 0.6 mm, a pair of 0.6 mm spacers 17 are appropriately mounted on surface 18.

It is appreciated that the LED is provided within a preferred embodiment, but that other types of a light source may be used for coupling to fiber 21.

Referring now to FIG. 4, circuit 26 includes an amplifier 31, to whose input PD 24 is connected, followed in order by synchronous detector 32, integrator 33 and comparator 34. Amplifier 31 amplifies the pulses induced in PD 24, then synchronous detector 32 multiplies them by a synchronous pulse train obtained from circuit 25. The latter operation is advantageously done in order to distinguish between reflected light pulses and any ambient light that may penetrate into fiber 22. The resultant signal is rectified, to produce a direct voltage. This voltage is integrated by integrator 33 over a certain time period—to yield a voltage value, which is compared in comparator 34 with a threshold value, resulting in a binary signal. This signal, which idicates whether or not light pulses have been reflected from fiber 21 into fiber 22 and, therefore—whether the proper connector is properly in place, is applied to other parts of the instrument, to accordingly enable or disable the operation of Crucial components, such as the fluid-drawing pump, and to turn a warning, or indicator, light on or off.

The threshold value is chosen to be such that would discriminate between integrated voltage values that result from specular reflection of light pulses from fiber 21 into fiber 22, as effected by end face 12 of a proper female connector 10 (that is, one that has been treated according to the present invention) properly placed, on the one hand, and values that result from diffuse reflection, such as may be effected by the uncoated and untreated end face of any other female connector (which is, therefore, considered to be an improper connector), or from an improperly placed proper connector, on the other hand.

It is appreciated that circuit 25 can also generate current waveforms other than pulses and that circuit 26 can detect resultant signals in a manner similar to that described hereabove or in any other manner known in the art. According to a refinement of the apparatus disclosed herein, there is placed an optical filter 27, which selectively transmits the band of wavelengths emitted by LED 23, either in front of fiber 22 within corresponding hole 15, or between fiber 22 and PD 24; this filter 27 is further instrumental in distinguishing between reflected light and ambient light.

According to an alternative configuration of the present invention, the reflective coating on end face 12 of female connector 10 is made to be spectrally selective, that is, it is made to reflect light of certain wavelengths or within a certain bandwidth. This can be achieved, for example, by having the reflective material itself contain dyes or pigments, or by coating the reflective layer with a suitable spectral filter. This configuration may be advantageously applied, for example, to discriminate between several subclasses of tube assemblies and matching each subclass to a corresponding type of analyzing instrument. For such an application, each type of instrument is provided with a light source having a unique spectral charcteristic and the reflection spectrum of each subclass of the tube assembly is made to match. Alternatively, the spectral bandwidth of the light source is broad and identical in all the types of instruments, but a filter in the path of the reflected light (as described above) is given a unique spectral charcteristic; according to one practical embodiment, this filter may be identical to the one placed over the reflective surface of the end face (as suggested above).

According to another alternative configuration of the present invention, end face 12 of female connector 10 is coated with a fluorescent or phosphorescent material, which is not necessarily specularly reflective. LED 23 is of a type that emits wavelengths short enough to stimulate fluorescence or phosphorescence in the material. There is placed an optical filter 27 either in front of fiber 22 within corresponding hole 15, or between fiber 22 and PD 24. The optical filter 27 selectively transmits the strongest wavelengths emitted by the fluorescent or phosphorescent material, while substantially attenuating wavelengths emitted by LED 23. The rest of the apparatus is as described hereabove. Although this configuration involves generally higher costs for treating the end of the connector than does the first configuration, it has two advantages:

(a) There is a high degree of discrimination between light reflected from a proper connector and light reflected from any other connector, since the optical filter 27 can be made to greatly attenuate the wavelength band emitted by LED 23 (which is the only band present in light reflected by improper connectors).

(b) Different types of fluorescent or phosphorescent materials, having different spectral emission characteristics (or spectral profile), can be chosen; these can be assigned to different classes of connectors for discrimination therebetween.

The second advantage can be realized, for example, by choosing for a particular instrument an optical filter 27 such that transmits one or more wavelengths at which the corresponding type of material emits strongly or strongest, while substantially attenuating those wavelengths at which all other types strongly emit. By properly adjusting the threshold level, this would result in an enabling signal being output by the comparator only when a connector of the corresponding class is properly connected to the instrument.

The fluorescent or phosphorescent material, rather than coated, or painted on the end face, may also be imbedded in the material of which the end face (or the entire connector) is formed. Another way of applying it to the end face is to bond or stamp (e.g. by hot-pressing) to the end face a foil or a film that contains such fluorescent or phosphorescent material.

According to a refinement of the alternative configuration, applicable in the case of phosphorescent materials, there is introduced a certain time delay between the train of current pulses applied to LED 23 and the synchronous pulse train obtained from circuit 25 and applied to the multiplier in circuit 26. The delay time is just greater than the duration of a pulse. The effect of the delay is that the detected light is only that which is emitted by the phosphorescence, excluding, in particular, directly reflected light. This feature further helps to discriminate between a proper connector and any other connector and may be used in addition to, or alternatively to, the above mentioned optical filter.

While the invention has been described with respect to a limited number of embodiments, it will be appreciated that many variations, modifications and other applications of the invention may be made.

What is claimed is:

1. Apparatus for analyzing fluid supplied to it through a tube, comprising:
   (a) an analyzing instrument;
   (b) a first connector attached to said tube and having an end face;
   (c) a second connector attached to said analyzing instrument;
   (d) a light source and a light receptor disposed such that when said first connector is correctly mated with said second connector, there is a clear optical path between at least one common point on said end face and each of said light source and said light receptor.

2. Apparatus for analyzing fluid according to claim 1, and wherein at least part of said end face is optically reflective.

3. Apparatus for analyzing fluid according to claim 1, and wherein at least part of said end face comprises a material selected from the group consisting of optically fluorescent and phosphorescent materials.

4. Apparatus for analyzing fluid according to claim 1, and wherein said light source comprises an end of an optical fiber having a source of light coupled to its other end.

5. Apparatus for analyzing fluid according to claim 1, and wherein said light receptor comprises an end of an optical fiber having an optical detector element coupled to its other end.

6. Apparatus for analyzing fluid according to claim 1, and wherein said light receptor comprises a detector element.

7. Apparatus for analyzing fluid according to claim 2 and wherein said at least part of said end face is such that it includes said at least one common point, when said first connector is properly mated with said second connector in any angular orientation.

8. Apparatus for analyzing fluid according to claim 2, and wherein said analyzing instrument is rendered operative only upon reception of an enabling signal, and further comprising an electric circuit responsive to light impinging on said light receptor, said circuit being configured so that only if a predetermined portion of light emitted from said light source is reflected by said at least part of said end face into said light receptor, does said circuit output said enabling signal to said analyzing instrument.

9. Apparatus for analyzing fluid according to claim 1, wherein said light source emits light in an essentially narrow band of wavelengths, and further comprising an optical filter, essentially transmissive to said band of wavelengths and disposed in said clear optical path.

10. Apparatus for analyzing fluid according to claim 3 and wherein said at least part of said end face is such that it includes said at least one common point, when said first connector is properly mated with said second connector in any angular orientation.

11. Apparatus for analyzing fluid according to claim 3, and wherein said light source emits light in a first band of wavelengths, such that stimulate said material to emit light in a second band of wavelengths, and further comprising an optical filter, essentially transmissive to at least one wavelength of said second band of wavelengths, and disposed in said clear optical path.

12. Apparatus for analyzing fluid according to claim 11, and wherein said material is one of a plurality of types, characterized in that said second band of wavelengths has a spectral profile essentially different among said plurality of types, and wherein said optical filter is essentially transmissive to one or more wavelengths at which said one of said plurality of types emits strongly and substantially attenuative to wavelengths at which any other of said types emits strongly.

13. Apparatus for analyzing fluid according to claim 3, and wherein said analyzing instrument is rendered operative only upon reception of an enabling signal, and further comprising an electric circuit responsive to light impinging on said light receptor, said circuit being configured so that only if a predetermined portion of light emitted from said material is collected by said light receptor, does said circuit output said enabling signal to said analyzing instrument.

14. Apparatus for analyzing fluid according to claim 13, wherein said light source emits light as a first train of pulses and said circuit further includes a synchronous detector that is fed with a multiplying signal formed as a second train of pulses, the two trains of pulses having equal rates and said second train being delayed with respect to said first train.

15. Apparatus for analyzing fluid according to claim 1, and wherein said light source emits light in pulses.

16. The apparatus of claim 1, wherein said at least part of said end face has spectrally selective reflectivity.

17. The apparatus of claim 16, wherein said light source emits light in a narrow band of wavelengths.

18. The apparatus of claim 16, and further comprising an optical filter having spectrally selective transmission and disposed in said clear optical path between said common point and said light receptor.

19. A system for verifying the proper connection of a tube assembly to a fluid analyzing instrument, the connection being effected by means of a first connector which is part of the tube assembly, and which has an end face, and a second connector, mating with the first connector and attached to said analyzing instrument, the system comprising light source and a light receptor disposed such that when said first connector is correctly mated with said second connector, there is a clear optical path between at least one common point on said end face and each of said light source and said light receptor.

20. The system of claim 19 and wherein at least part of said end face is optically reflective.

21. The system of claim 19 and wherein at least part of said end face comprises a material selected from the group consisting of optically fluorescent and phosphorescent materials.

22. The system of claim 19 and wherein said light source comprises an end of an optical fiber having a source of light coupled to its other end.

23. The system of claim 19 and wherein said light receptor comprises an end of an optical fiber having an optical detector element coupled to its other end.

24. The system of claim 19 and wherein said light receptor comprises a detector element.

25. The system of claim 19, and wherein said at least part of said end face is such that it includes said at least one common point, when said first connector is properly mated with said second connector in any angular orientation.

26. The system of claim 20, and wherein said analyzing instrument is rendered operative only upon reception of an enabling signal, and further comprising an electric circuit responsive to light impinging on said light receptor, said circuit being configured so that only if a predetermined portion of any light emitted from said light source is reflected by said at least part of said end face into said light receptor, does said circuit output said enabling signal to said analyzing instrument.

27. The system of claim 19, wherein said light source emits light in an essentially narrow band of wavelengths, and further comprising an optical filter, essentially transmissive to said band of wavelengths and disposed in said clear optical path.

28. The system of claim 21, and wherein said at least part of said end face is such that it includes said at least one common point, when said first connector is properly mated with said second connector in any angular orientation.

29. The system of claim 28, wherein said light source emits light in a first band of wavelengths, such that stimulate said material to emit light in a second band of wavelengths, and further comprising an optical filter, essentially transmissive to at least one wavelength of said second band and disposed in said clear optical path.

30. The system of claim 29, wherein said material is one of a plurality of types, characterized in that said second band of wavelengths has a spectral profile essentially different among said plurality of types, and wherein said optical filter is essentially transmissive to one or more wavelengths at which said one of said plurality of types emits strongly and substantially attenuative to wavelengths at which any other of said types emits strongest.

31. The system of claim 21, wherein said analyzing instrument is rendered operative only upon reception of an enabling signal and further comprising an electric circuit responsive to light impinging on said light receptor, said circuit being configured so that only if a predetermined portion of any light emitted from said material is collected by said light receptor does said circuit output said enabling signal to said analyzing instrument.

32. The system of claim 31, wherein said light source emits light as a first train of pulses and said circuit further includes a synchronous detector that is fed with a multiplying signal formed as a second train of pulses, the two trains of pulses having equal rates and said second train being delayed with respect to said first train.

33. The system of claim 19, wherein said light source emits light in pulses.

34. The system of claims 20, wherein said at least part of said end face has spectrally selective reflectivity.

35. The system of claim 34, wherein said light source emits light in a narrow band of wavelengths.

36. The system of claim 34, further comprising an optical filter having a spectrally selective transmission and disposed in said clear optical path between said common point and said light receptor.

37. A system for verifying the class of a tube assembly connected to a fluid analyzer, the connection being effected by means of a first connector which is part of the tube assembly and which has an end face, and a second connector, mating with the first connector and attached to said analyzing instrument, the system comprising a light source and a light receptor disposed such that when said tube assembly is of the correct class, and when said first connector is correctly mated with said second connector, optical identifying information may be transferred along a clear optical path between at least one common point on said end face and each of said light source and said light receptor.

38. The system of claim 37 and wherein at least part of said end face is optically reflective.

39. The system of claim 37 and wherein at least part of said end face comprises a material selected from the group consisting of optically fluorescent and phosphorescent materials.

40. The system of claim 37 and wherein said light source comprises an end of an optical fiber having a source of light coupled to its other end.

41. The system of claim 37 and wherein said light receptor comprises an end of an optical fiber having an optical detector element coupled to its other end.

42. The system of claim 37 and wherein said light receptor comprises a detector element.

43. The system of claim 37, and wherein said analyzing instrument is rendered operative only upon reception of an enabling signal, and further comprising an electric circuit responsive to light impinging on said light receptor, said circuit being configured so that only if correct optical identifying information from said light source is reflected by said at least part of said end face into said light receptor, does said circuit output said enabling signal to said analyzing instrument.

44. The system of claim 37, wherein said light source emits light in an essentially narrow band of wavelengths, and further comprising an optical filter, essentially transmissive to said band of wavelengths and disposed in said clear optical path.

45. The system of claim 39 wherein said light source emits light in a first band of wavelengths, such that stimulate said material to emit light in a second band of wavelengths, and further comprising an optical filter, essentially transmissive to at least one wavelength of said second band and disposed in said clear optical path.

46. The system of claim 45, wherein said material is one of a plurality of types, characterized in that said second band of wavelengths has a spectral profile essentially different among said plurality of types, and wherein said optical filter is essentially transmissive to one or more wavelengths at which said one of said plurality of types emits strongly and substantially attenuative to wavelengths at which any other of said types emits strongest.

47. The system of claim 39, wherein said analyzing instrument is rendered operative only upon reception of an enabling signal, and further comprising an electric circuit responsive to light impinging on said light receptor, said circuit being configured so that only if correct optical identifying information is transferred from said light source to said light receptor, does said circuit output said enabling signal to said analyzing instrument.

48. The system of claim 47, wherein said light source emits light as a first train of pulses and said circuit further includes a synchronous detector that is fed with a multiplying signal formed as a second train of pulses, the two trains of pulses having equal rates and said second train being delayed with respect to said first train.

49. The system of claim 37, wherein said light source emits light in pulses.

50. The system of claim 37, wherein said at least part of said end face has spectrally selective reflectivity.

51. The system of claim 50, wherein said light source emits light in a narrow band of wavelengths.

52. The system of claim 50, further comprising an optical filter having a spectrally selective transmission and disposed in said clear optical path between said common point and said light receptor.

53. A method for verifying the proper connection of a tube to a fluid analyzing instrument, the connection being effected by means of a first connector attached to the tube and having an end face, and a second connector mating with said first connector and attached to said analyzing instrument, the method comprising the step of providing a light source and a light receptor disposed such that when said first connector is correctly mated with said second connector, there is a clear optical path between at least one common point on said end face and each of said light source and said light receptor.

54. The method of claim 53, and further comprising the step of making at least part of said end face optically reflective.

55. The method of claim 53, and further comprising the step of making at least part of said end face of a material selected from the group consisting of optically fluorescent and phosphorescent materials.

56. The method of claim 53 and wherein said light source comprises an end of an optical fiber having a source of light coupled to its other end.

57. The method of claim 53 and wherein said light receptor comprises an end of an optical fiber having an optical detector element coupled to its other end.

58. The method of claim 53 and wherein said light receptor comprises detector element.

59. The method of claim 53 and wherein said at least part of said end face is such that it includes said at least one common point, when said first connector is properly mated with said second connector in any angular orientation.

60. The method of claim 54 wherein said analyzing instrument is rendered operative only upon reception of an enabling signal, and further comprising the step of providing an electric circuit responsive to light impinging on said light receptor, said circuit being configured so that only if a predetermined portion of light emitted from said light source is reflected by said at least part of said end face into said light receptor, does said circuit output said enabling signal to said analyzing instrument.

61. The method of claim 53 wherein said light source emits light in an essentially narrow band of wavelengths, and further comprising the step of providing an optical filter, essentially transmissive to said band of wavelengths and disposed in said clear optical path.

62. The method of claim 55 and wherein said at least part of said end face is such that it includes said at least one common point, when said first connector is properly mated with said second connector in any angular orientation.

63. The method of claim 55, whereby said light source is made to emit light in a first band of wavelengths, such that stimulate said material to emit light in a second band of wavelengths, and further comprising the step of providing an optical filter, essentially transmissive to at least one wavelength of said second band and disposed in said clear optical path.

64. The method of claim 63, whereby said material is chosen to be one of a plurality of types, characterized in that said second band of wavelengths has a spectral profile essentially different among said plurality of types, and whereby said optical filter is made to be essentially transmissive to one or more wavelengths at which said one of said plurality of types emits strongly and substantially attenuative to wavelengths at which any other of said types emits strongest.

65. The method of claims 55, wherein said analyzing instrument is rendered operative only upon reception of an enabling signal, and further comprising the step of providing an electric circuit responsive to light impinging on said light receptor, said circuit being configured so that only if a predetermined portion of any light emitted from said material is collected by light receptor does said circuit output said enabling signal to said analyzing instrument.

66. The method of claim 65, whereby said light source is made to emit light as a first train of pulses, said circuit is made to include a synchronous detector and said synchronous detector is fed with a multiplying signal formed as a second train of pulses, the two trains of pulses having equal rates and said second train being delayed with respect to said first train.

67. The method of claim 53, whereby said light source is made to emit light in pulses.

68. The method of claim 54, and whereby said at least part of said end face is made to have spectrally selective reflectivity.

69. The method of claim 68, whereby said light source is made to emit light in a narrow band of wavelengths.

70. The method of claim 68, and further comprising the step of providing an optical filter having a spectrally selective transmission and disposing it in said clear optical path between said common point and said light receptor.

71. A method for verifying the class: of a connection tube connected to a fluid analyzer, the connection being effected by means of a first connector which is part of said tube assembly and which has an end face, and a second connector mating with said first connector and attached to said analyzing instrument, the method comprising the step of providing a light source and a light receptor disposed such that when said tube assembly is of the correct class, optical identifying information may be transferred along a clear optical path between at least one common point on said end face and each of said light; source and said light receptor.

72. The method of claim 71, and further comprising the step of making at least part of said end face optically reflective.

73. The method of claim 71, and further comprising the step of making at least part of said end face of a material selected from the group consisting of optically fluorescent and phosphorescent materials.

74. The method of claim 72, and whereby said at least part of said end face is made to have spectrally selective reflectivity.

75. The method of claim 74, whereby said light source is made to emit light in a narrow band of wavelengths.

76. The method of claim 74, and further comprising the step of providing an optical filter having a spectrally selective transmission and disposing it in said clear optical path between said common point and said light receptor.

77. A tube assembly for connection to a fluid analyzing instrument, comprising a connector having an end face, wherein at least part of said end face comprises a material selected from the group consisting of optically fluorescent and phosphorescent materials.

78. The tube assembly of claim 77, wherein said material is any one of a plurality of types, characterized by different spectra of emission.

79. The tube assembly of claim 77, wherein said material is deposited on said end face.

80. The tube assembly of claim 77, wherein said material is on an object attached to said end face.

81. The tube assembly of claim 77, wherein said material is imbedded in said end face.

82. A tube assembly for connection to a fluid analyzing instrument, comprising a connector, said connector having an end face, and wherein at least part of said end face is formed with a reflective foil attached thereto.

83. A tube assembly for connection to a fluid analyzing instrument, comprising a connector, said connector having an end face, and wherein at least part of said end face is formed with a reflective material deposited thereon.

84. A tube assembly for connection to a fluid analyzing instrument, comprising a connector, said connector having an end face, and wherein said at least part of said end face is formed with a reflective object bonded to said end face.

85. A tube assembly for connection to a fluid analyzing instrument, comprising a connector, said connector having an end face, and wherein said at least part of said end face has spectrally selective reflectivity.

86. A tube assembly for connection to a fluid analyzing instrument, comprising a connector, said connector having an end face, at least part of said end face being optically reflective, and further comprising an optical filter having spectrally selective transmission, disposed over said at least part of said end face.

* * * * *

(12) EX PARTE REEXAMINATION CERTIFICATE (9420th)
United States Patent
Colman et al.

(10) Number: US 6,437,316 C1
(45) Certificate Issued: Nov. 21, 2012

(54) FLUID ANALYZER WITH TUBE CONNECTOR VERIFIER

(75) Inventors: Joshua L. Colman, Ramat Shlomo (IL); Amnon Menachem, Jerusalem (IL)

(73) Assignee: Spegas Industries Ltd., Jerusalem (IL)

Reexamination Request:
No. 90/012,278, May 23, 2012

Reexamination Certificate for:
Patent No.: 6,437,316
Issued: Aug. 20, 2002
Appl. No.: 08/961,013
Filed: Oct. 30, 1997

(30) Foreign Application Priority Data

Nov. 4, 1996 (IL) .......................................... 119562

(51) Int. Cl.
*G01N 1/02* (2006.01)
*G01N 35/00* (2006.01)
*A61M 39/10* (2006.01)
*A61M 39/00* (2006.01)
*B01L 3/00* (2006.01)

(52) U.S. Cl. ................................. 250/222.1; 250/559.3
(58) Field of Classification Search ....................... None
See application file for complete search history.

(56) References Cited

To view the complete listing of prior art documents cited during the proceeding for Reexamination Control Number 90/012,278, please refer to the USPTO's public Patent Application Information Retrieval (PAIR) system under the Display References tab.

*Primary Examiner* — Cheng-Yuan Tseng

(57) ABSTRACT

Apparatus for analyzing fluid supplied to it through a tube, comprising an analyzing instrument within an enclosure, a first connector attached to the tube and having an end face, a second connector, mating with the first connector and attached to the enclosure, a pair of optical fibers disposed inside the enclosure, a first end of each of the fibers is mounted in the second connector, there is a clear optical path between the end face of each of the first ends of the fibers and at least one common point on the end face. A light source is optically coupled to the second end of a first one of the pair of fibers, and a light detector optically coupled to the second end of the second one of the pair of fibers.

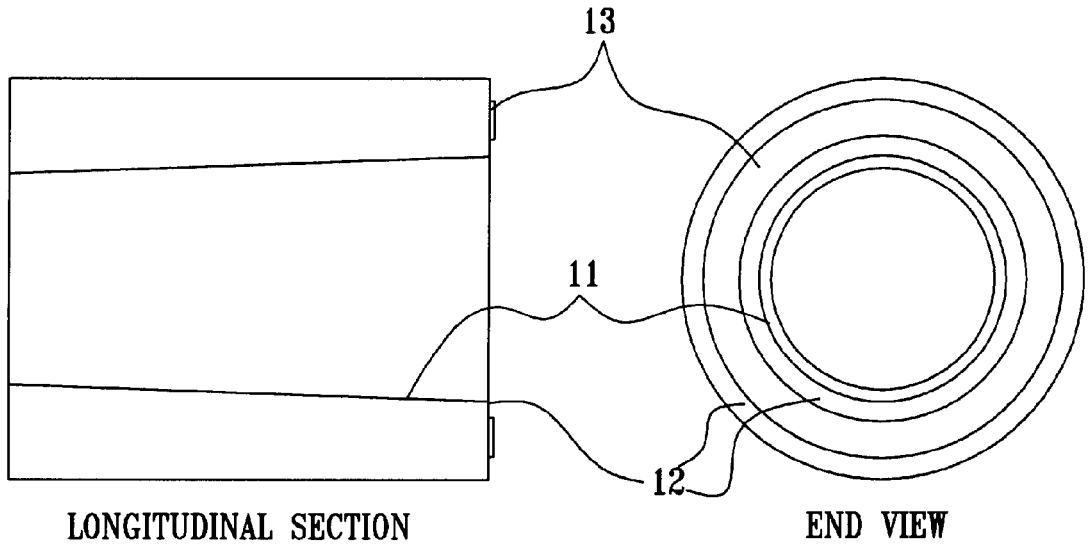

LONGITUDINAL SECTION · END VIEW

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-2, 4-8, 19-20, 22-26, 37-38, 40-43, 53-54, 56-60 and 71-72 is confirmed.

Claims 82-84 are determined to be patentable as amended.

New claims 87-124 are added and determined to be patentable.

Claims 3, 9-18, 21, 27-36, 39, 44-52, 55, 61-70, 73-81 and 85-86 were not reexamined.

82. A tube assembly for connection to a fluid analyzing instrument, comprising a connector, said connector having *a tapered inner wall and* an *annular* end face, and wherein at least part of said end face is formed with a reflective foil attached thereto *and wherein said connector is configured to connect the tube assembly to the fluid analyzing instrument*.

83. A tube assembly for connection to a fluid analyzing instrument, comprising a connector, said connector having *a tapered inner wall and* an *annular* end face, and wherein at least part of said end face is formed with a reflective material deposited thereon *and wherein said connector is configured to connect the tube assembly to the fluid analyzing instrument*.

84. A tube assembly for connection to a fluid analyzing instrument, comprising a connector, said connector having *a tapered inner wall and* an *annular* end face, and wherein said at least part of said end face is formed with a reflective object bonded to said end face *and wherein said connector is configured to connect the tube assembly to the fluid analyzing instrument*.

*87. The tube assembly of claim 82, wherein said connector is configured to connect said tube assembly to said fluid analyzing instrument at a plurality of angular orientations.*

*88. The tube assembly of claim 82, wherein said connector is configured to connect said tube assembly to said fluid analyzing instrument at any angular orientation.*

*89. The tube assembly of claim 82, wherein said connector comprises a luer connector.*

*90. The tube assembly of claim 82, wherein said fluid analyzing instrument comprises a capnograph.*

*91. The tube assembly of claim 82, wherein the connector comprises a fluid passage having an opening through the annular end face.*

*92. The tube assembly of claim 91, wherein the reflective foil comprises a ring around the opening.*

*93. The tube assembly of claim 82, further comprising a tube attached to the connector for fluid flow to the fluid analyzing instrument.*

*94. The tube assembly of claim 83, wherein said connector is configured to connect said tube assembly to said fluid analyzing instrument at a plurality of angular orientations.*

*95. The tube assembly of claim 83, wherein said connector is configured to connect said tube assembly to said fluid analyzing instrument at any angular orientation.*

*96. The tube assembly of claim 83, wherein said connector comprises a luer connector.*

*97. The tube assembly of claim 83, wherein said fluid analyzing instrument comprises a capnograph.*

*98. The tube assembly of claim 83, wherein said connector is formed from said reflective material.*

*99. The tube assembly of claim 98, wherein said reflective material is made reflective by polishing.*

*100. The tube assembly of claim 83, wherein the connector comprises a fluid passage having an opening through the annular end face.*

*101. The tube assembly of claim 100, wherein the reflective material comprises a ring around the opening.*

*102. The tube assembly of claim 83, further comprising a tube attached to the connector for fluid flow to the fluid analyzing instrument.*

*103. The tube assembly of claim 84, wherein said connector is configured to connect said tube assembly to said fluid analyzing instrument at a plurality of angular orientations.*

*104. The tube assembly of claim 84, wherein said connector is configured to connect said tube assembly to said fluid analyzing instrument at any angular orientation.*

*105. The tube assembly of claim 84, wherein said connector comprises a luer connector.*

*106. The tube assembly of claim 84, wherein said fluid analyzing instrument comprises a capnograph.*

*107. The tube assembly of claim 84, wherein said connector and said reflective object comprise the same reflective material.*

*108. The tube assembly of claim 107, wherein said reflective material is made reflective by polishing.*

*109. The tube assembly of claim 84, wherein the connector comprises a fluid passage having an opening through the annular end face.*

*110. The tube assembly of claim 109, wherein the reflective object comprises a ring around the opening.*

*111. The tube assembly of claim 84, further comprising a tube attached to the connector for fluid flow to the fluid analyzing instrument.*

*112. The tube assembly of claim 84, wherein said connector and said reflective object are integrally bonded.*

*113. The apparatus for analyzing fluid of claim 1, wherein said end face is annular.*

*114. The apparatus for analyzing fluid of claim 113, wherein the first connector comprises a fluid passage having an opening through the annular end face.*

*115. The apparatus for analyzing fluid of claim 1, wherein said first connector is configured to connect to said second connector at a plurality of angular orientations.*

*116. The apparatus for analyzing fluid of claim 1, wherein said first connector is configured to connect to said second connector at any angular orientation.*

*117. The apparatus for analyzing fluid of claim 1, wherein said first connector comprises a luer connector comprising a tapered inner wall.*

*118. The apparatus for analyzing fluid of claim 1, wherein said analyzing instrument comprises a capnograph.*

*119. The apparatus for analyzing fluid of claim 1, wherein said first connector comprises a tapered inner wall and an annular end face, and wherein at least part of said end face is formed with a reflective foil attached thereto, and wherein said first connector is configured to connect the tube to the analyzing instrument.*

120. The apparatus for analyzing fluid of claim 1, wherein said first connector comprises a tapered inner wall and an annular end face, and wherein at least part of said end face is formed with a reflective material deposited thereon, and wherein said first connector is configured to connect the tube to the analyzing instrument.

121. The apparatus for analyzing fluid of claim 1, wherein said first connector comprises a tapered inner wall and an annular end face, and wherein said at least part of said end face is formed with a reflective object bonded to said end face, and wherein said first connector is configured to connect the tube to the analyzing instrument.

122. The apparatus for analyzing fluid of claim 2, wherein said end face is annular.

123. The apparatus for analyzing fluid of claim 122, wherein the first connector comprises a fluid passage having an opening through the annular end face.

124. The apparatus for analyzing fluid of claim 123, wherein said at least part of said end face comprises a ring around the opening.

* * * * *